United States Patent
Schneider et al.

(10) Patent No.: US 7,507,818 B2
(45) Date of Patent: *Mar. 24, 2009

(54) METHOD FOR THE PRODUCTION OF ALKOXYCARBONYLAMINOTRIAZINES

(75) Inventors: Joerg Schneider, Weinheim (DE); Guenter Scherr, Ludwigshafen (DE); Hans Schupp, Worms (DE); Andreas Eichfelder, Maxdorf (DE); Alain Robert, Niederkirchen (DE); Martin Reif, Roemerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/539,076

(22) PCT Filed: Dec. 16, 2003

(86) PCT No.: PCT/EP03/14274

§ 371 (c)(1),
(2), (4) Date: Jun. 15, 2005

(87) PCT Pub. No.: WO2004/054990

PCT Pub. Date: Jul. 1, 2004

(65) Prior Publication Data

US 2006/0069254 A1    Mar. 30, 2006

(30) Foreign Application Priority Data

Dec. 18, 2002   (DE) .................... 102 59 672

(51) Int. Cl.
*C07D 251/70*  (2006.01)
*C07D 251/50*  (2006.01)
*C07D 251/48*  (2006.01)
*C07D 251/18*  (2006.01)

(52) U.S. Cl. ...................... 544/196; 544/200
(58) Field of Classification Search ............. 544/196, 544/200
See application file for complete search history.

(56) References Cited

U.S. PATENT DOCUMENTS 7,169,923 B2 *  1/2007  Schneider et al. .......... 544/196

FOREIGN PATENT DOCUMENTS

DE        92 535    5/1897
EP     0 624 577   11/1994

OTHER PUBLICATIONS

Finke, Richard G. et al.: "Model Studies of Coenzyme B12 Dependent Diol Dehydratase 1.1 Synthetic, Physical Property, and Product Studies of Two Key, Cobalt-Bound, Putative Diol Dehdratase Intermediates" Journal of the American Chemical Society, vol. 105, No. 26, pp. 7592-7604. 1983. XP-002277223.

* cited by examiner

*Primary Examiner*—Venkataraman Balasubramanian
(74) *Attorney, Agent, or Firm*—Oblon, Spivak, McClelland, Maier & Neustadt, P.C.

(57) ABSTRACT

In a process for preparing alkoxycarbonylaminotriazines, di- or triaminotriazines are reacted with cyclic carbonic esters and optionally with minor amounts of acyclic carbonic esters in the presence of an alcohol and of an alkali metal alkoxide or alkaline earth metal alkoxide as a base.

10 Claims, No Drawings

METHOD FOR THE PRODUCTION OF ALKOXYCARBONYLAMINOTRIAZINES

The present invention relates to a novel process for preparing alkoxycarbonylaminotriazines by reacting di- or triaminotriazines with cyclic carbonic esters and optionally with minor amounts of acyclic carbonic esters, in the presence of an alkanol and of an alkali metal alkoxide or alkaline earth metal alkoxide as a base.

EP-A-624 577 discloses the preparation of alkoxycarbonylaminotriazines by reacting triazines, for example melamine, with acyclic carbonic esters in the presence of a base. In general, melamine is reacted there with a carbonic ester, e.g. dimethyl carbonate, in the presence of the parent alkanol of the carbonic ester, in this case methanol, for example, and in the presence of an alkali metal alkoxide based on the parent alkanol of the carbonic ester, in this case methanol, for example, as a base. The reaction is also described of melamine, for example, with dimethyl carbonate in the presence of a higher alcohol, for example butanol or 2-ethylhexanol, and of the corresponding sodium alkoxide, in this case sodium butoxide or sodium 2-ethylhexoxide, for example, as a base.

Those skilled in the art are taught in EP-A-624 577 that the process described there can be carried out exclusively with acyclic carbonic esters.

It is an object of the present invention to provide a novel process for preparing alkoxycarbonylaminotriazines which can be carried out in a simple manner and which allows the preparation of a large spectrum of mixtures of mixed-functionality and/or isomeric alkoxycarbonylaminotriazines in high yield and purity by means of the industrially readily obtainable cyclic carbonic esters.

We have found that this object is achieved, advantageously, by the preparation of alkoxycarbonylaminotriazines of the formula I

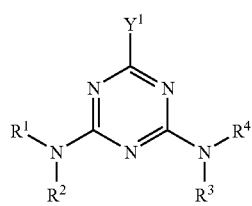

in which
$Y^1$ is hydrogen, $C_1$-$C_4$-alkyl, phenyl optionally substituted by $C_1$-$C_4$-alkyl, $C_1$-$C_4$-alkoxy or halogen, or a radical of the formula $NR^5R^6$ and
$R^1, R^2, R^3, R^4, R^5$ and $R^6$ are each independently hydrogen or a radical of the formula COOX or X where X is $C_1$-$C_{13}$-alkyl whose carbon framework may be interrupted by 1 or 2 oxygen atoms in an ether function and/or be substituted by hydroxyl, or $C_3$-$C_6$-alkenyl, with the proviso that at least one of the radicals $R^1$ to $R^4$ in formula I or, when $Y^1$ is $NR^5R^6$, at least one of the radicals $R^1$ to $R^6$ is COOX, by reacting a triazine of the formula II

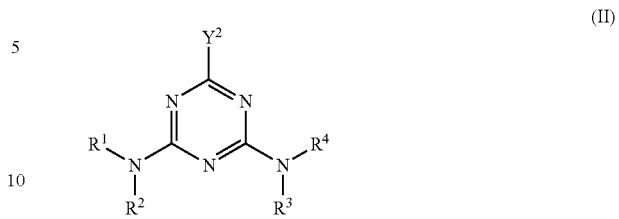

in which
$Y^2$ is hydrogen, $C_1$-$C_4$-alkyl, amino or phenyl optionally substituted by $C_1$-$C_4$-alkyl, $C_1$-$C_4$-alkoxy or halogen, and
$R^1$ to $R^4$ are each as defined above, with the proviso that, in formula II, when $Y^2$ is not amino, at least one of the radicals $R^1$ to $R^4$ is hydrogen, with carbonic esters in the presence of an alcohol and of a base, which comprises reacting the triazine of the formula II with a cyclic carbonic ester of the formula III

in which
L is ethylene, 1,2- or 1,3-propylene, or 1,2-, 1,4-, 2,3-, or 1,3-butylene, and also optionally with minor amounts of an acyclic carbonic ester of the formula IV

$$Z^1O\text{—}CO\text{—}OZ^2 \quad (IV),$$

in which
$Z^1$ and $Z^2$ are each independently $C_1$-$C_8$-alkyl, and a $C_1$-$C_{13}$-alkanol whose carbon framework may be interrupted by 1 or 2 oxygen atoms in an ether function and/or be substituted by hydroxyl, or a $C_3$-$C_6$-alkenol, in the presence of an alkali metal alkoxide or alkaline earth metal alkoxide as a base.

All the alkyl radicals contained in the formulae listed here may be either straight-chain or branched.

$Y^1, Y^2, X, Z^1$ and $Z^2$ radicals are, for example, methyl, ethyl, propyl, isopropyl, butyl, isobutyl, sec-butyl or tert-butyl.

$X, Z^1$ and $Z^2$ radicals are also, for example, pentyl, isopentyl, neopentyl, tert-pentyl, hexyl, 2-methylpentyl, heptyl, octyl, 2-ethylhexyl and isooctyl.

X radicals are also, for example, nonyl, isononyl, decyl, isodecyl, undecyl, dodecyl, tridecyl, isotridecyl, 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 4-methoxybutyl, 2- or 4-ethoxybutyl, 3,6-dioxaheptyl, 3,6-dioxaoctyl, 3,7-dioxaoctyl, 4,7-dioxaoctyl, 2- or 3-butoxypropyl or 2,4-butoxybutyl, 2-hydroxyethyl, 2- or 3-hydroxypropyl, 2- or 4-hydroxybutyl, 3-hydroxybut-2-yl, allyl, methallyl, ethallyl, 2-, 3- or 4-penten-1-yl or 2-, 3-, 4- or 5-hexen-1-yl. (The above terms isooctyl, isononyl, isodecyl and isotridecyl are trivial names and stem from the alcohols obtained by the oxo process—on this subject, cf. Ullmann's Encyclopedia of Industrial Chemistry, 5th Edition, Vol. A 1, pages 290 to 293, and also Vol. A 10, pages 284 and 285.)

$Y^1$ and $Y^2$ radicals are also, for example, phenyl, 2-, 3- or 4-methylphenyl, 2-, 3- or 4-ethylphenyl, 2,4-dimethylphenyl, 2-, 3- or 4-methoxyphenyl, 2-, 3- or 4-ethoxyphenyl, 2,4-dimethoxyphenyl, 2-, 3- or 4-fluorophenyl or 2-, 3- or 4-chlorophenyl.

Suitable alkanols which may find use in the process according to the invention are, for example, methanol, ethanol, propanol, isopropanol, butanol, isobutanol, sec-butanol, tert-butanol, pentanol, isopentanol, neopentanol, tert-pentanol, hexanol, 2-methylpentanol, heptanol, octanol, 2-ethylhexanol, isooctanol, nonanol, isononanol, decanol, isodecanol, undecanol, dodecanol, tridecanol, isotridecanol, 2-methoxyethanol, 2-ethoxyethanol, 2-propoxyethanol, 2-butoxyethanol, 2- or 3-methoxypropanol, 2- or 3-ethoxypropanol, 2- or 3-propoxypropanol, 2- or 4-methoxybutanol, 2- or 4-ethoxybutanol, 3,6-dioxaheptanol, 3,6-dioxaoctanol, 3,7-dioxaoctanol, 4,7-dioxaoctanol, 2- or 3-butoxypropanol, 2- or 4-butoxybutanol, ethane-1,2-diol, propane-1,2-diol, propane-1,3-diol, 3-oxa-5-hydroxypentanol, 3,6-dioxa-8-hydroxyoctanol, 3-oxa-5-hydroxy-2,5-dimethylpentanol or 3,6-dioxa-8-hydroxy-2,5,8-trimethyloctanol.

Suitable $C_3$-$C_6$-alkenols which may find use in the process according to the invention are, for example, allyl alcohol, methallyl alcohol, ethallyl alcohol, 2-, 3- or 4-penten-1-ol or 2-, 3-, 4- or 5-hexen-1-ol.

Preference is given to using $C_1$-$C_{13}$-alkanols, and particular mention is to be made of the use of $C_1$-$C_7$-alkanols.

The alcohols used in the process according to the invention may find use either individually or as a mixture with each other. In the latter case, the number of mixing partners and also the mixing ratios may be as desired.

When alkanol or alkoxide are mentioned hereinbelow, these terms also include the abovementioned alkenols or alkenolates.

Suitable alkali metal alkoxides or alkaline earth metal alkoxides which may find use in accordance with the invention are, for example, the lithium, sodium, potassium, magnesium or calcium salts of the alkanols described in detail above. Preference is given to the use of alkali metal methoxides, in particular of sodium methoxide.

Alkali metal alkoxide or alkaline earth metal alkoxide may find use either in the solid state or in dissolved or suspended form.

Preferred solvents/diluents are in this case in particular the alcohols described in detail above, alone or as a mixture with each other. However, other customary inert diluents which are known per se may also find use.

A procedure using a catalyst is likewise possible.

For example, phase transfer catalysts of the type as described, for example, in Ullmann's Encyclopedia of Industrial Chemistry, 5th Edition, Vol. A 19, pages 239 to 248, may be used.

Further catalysts may be metal salts or complexes, preferably oxides, chalcogenates, carbonates or halides of the alkali metals, alkaline earth metals or transition metals. Particular mention should be made here of, for example, lithium chloride, magnesium chloride and sodium carbonate.

In the process according to the invention, for one molar equivalent of amino groups in the triazine of the formula II, generally from 1 to 50 mol, preferably from 3 to 30 mol, of alkanol are used.

In addition, in the process according to the invention, for one molar equivalent of amino groups in the triazine of the formula II, generally from 0.1 to 10 mol, preferably from 1 to 3 mol, of cyclic carbonic ester of the formula III are used.

In addition, in the process according to the invention, for one molar equivalent of amino groups in the triazine of the formula II, generally from 0.1 to 10 molar equivalents, preferably from 1 to 7 molar equivalents, of alkali metal alkoxide or alkaline earth metal alkoxide are used.

If the process according to the invention is carried out in the presence of a catalyst, generally from $10^{-10}$ to 10% by weight, preferably from $10^{-3}$ to 1% by weight, of catalyst, based in each case on the weight of the triazine of the formula II, are used.

The process according to the invention is generally carried out at a temperature of from 20 to 180° C., preferably from 50 to 120° C.

It is customary to work under atmospheric pressure, although it is possible to employ elevated pressure, generally up to 8 bar.

The process according to the invention is carried out with cyclic carbonic esters of the formula III and also optionally with minor amounts of acyclic carbonic esters. For the inventive purpose, minor amounts means that up to 30 mol % of the cyclic carbonic esters of the formula III may be replaced by acyclic carbonic esters of the formula IV.

Preference is given to a procedure in which from 0 to 25 mol %, preferably from 0 to 10 mol %, of the cyclic carbonic esters of the formula III may be replaced by acyclic carbonic esters of the formula IV.

If acyclic carbonic esters of the formula IV also find use in the process according to the invention, preference is given to those in which $Z^1$ and $Z^2$ are each independently $C_1$-$C_4$-alkyl.

Of particular interest is the use of triazines of the formula II in which $Y^2$ is amino as the reactant in the process according to the invention, and particular emphasis is given to the use of melamine (2,4,6-triamino-1,3,5-triazine).

Of particular interest is also the use of a cyclic carbonic ester of the formula III in which L is ethylene or 1,2-propylene, in particular ethylene.

Of very particular-interest is the preparation of alkoxycarbonylaminotriazines of the formula V

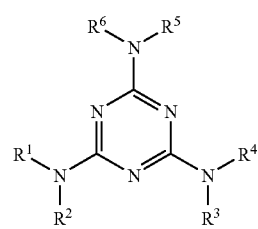

in which $R^1$ to $R^6$ are each as defined above, with the proviso that three of these radicals are each hydrogen and the remaining three of these radicals are each a radical of the formula COOX where X is as defined above, by means of the process according to the invention.

The alkoxycarbonylaminotriazines according to the invention can be prepared in various variants (A-F).

Advantageously, the process according to the invention is carried out in such a way that triazine II and alkanol are initially charged and then, in any desired sequence, alkali metal alkoxide or alkaline earth metal alkoxide, in the solid state and/or dissolved in alkanol, and carbonic ester are metered in, and alkali metal alkoxide or alkaline earth metal alkoxide and carbonic ester can be metered in fully before the commencement of the reaction or partly before the commencement of the reaction and partly after the commencement of the reaction. Distilling off certain amounts of alkanol from the reaction mixture before and/or during the reaction can be used to attain desired alkanol ratios.

In variant A), triazine II, alkanol and the dissolved alkali metal alkoxide or alkaline earth metal alkoxide are combined, and carbonic ester is subsequently added at elevated temperature (generally from 30 to 85° C.).

In variant B), all components are initially charged before commencement of the reaction.

In variant C), triazine II, alkanol and carbonic ester are initially charged and a portion of the alkali metal alkoxide or alkaline earth metal alkoxide, which is partly in dissolved and partly in solid state, is metered in before the commencement of the reaction and the remainder after the commencement of the reaction.

In variant D), triazine II, alkanol and carbonic ester are initially charged, and a portion of the alkali metal alkoxide or alkaline earth metal alkoxide, which is either in dissolved form or in a solid state, is metered in before the commencement of the reaction and the remainder after the commencement of the reaction.

In variant E), catalysts are added before or during the reaction.

In variant F), different alkali metal alkoxides (e.g. lithium alkoxide and sodium alkoxide) are added before or during the reaction.

Otherwise, the reaction can also be conducted in such a way that melamine is metered in in stages or continuously during the reaction.

The process according to the invention can be carried out in customary reaction apparatus, for example a tank or tubular reactor. When the novel process is carried out in such a way that the triazine of the formula II:alkanol molar ratio is very high, preference is given to the use of apparatus having mixing action in the case of highly viscous or inhomogeneous reaction mixtures, for example kneading reactors. It is also possible to use self-cleaning apparatus having mixing action. Such apparatus is known per se and commercially available. Suitable reactors of this type are, for example, the chamber reactor, the circulation reactor or the screw reactor.

Advantageously, the workup of the resulting reaction mixture takes place in the absence of additional solvent.

To this end, the alkanolic reaction mixture is contacted directly with acid, either by metering in acid or by transferring the reaction mixture into a suitable acid.

The acid can be added in concentrated form, and water can be added during or after the metered addition of the acid. Especially when aqueous or highly concentrated acids are used, suitable mixing has to be ensured during the metered addition. The reaction mixture can be acidified using all customary and industrially available organic and inorganic acids in any desired concentration, preferably as from 30 to 85% by weight aqueous solutions. Preference is given to using mineral acids whose salts have a high water solubility, such as nitric acid, sulfuric acid or phosphoric acid, but mention should also be made here of the carboxylic acid formic acid.

After the addition of acid to the reaction mixture, an aqueous phase possibly also comprising the diols of the formula HO-L-OH in which L is as defined above and an alkanolic phase which are separated from one another are formed. The separation of the phases is temperature- and pH-dependent, so that additional water is added at a temperature of from 10 to 70° C., preferably from 15 to 50° C., and at a pH of from 0 to 8, preferably from 2 to 5.

The target products result directly as a from 10 to 80% by weight alkanolic solution. Subsequent concentration of the alkanolic phase simultaneously removes some entrained water azeotropically, (for example in the case of butanol), so that further drying steps, for example the addition of drying agents, are not required.

It will be appreciated that the reaction mixture, after neutralization with any desired acid, can also be worked up by extraction, washing and/or by filtration.

The novel process, which can be carried out either in a continuous or batchwise procedure, affords the target products in high yield and purity. A further advantage of the process according to the invention is the use of cyclic carbonic esters which, compared to the acyclic carbonic esters, may be regarded as harmless with regard to safety.

The alkoxycarbonylaminotriazines obtainable by means of the process according to the invention are valuable paint raw materials.

The examples which follow illustrate the invention.

All reactions were carried out with the exclusion of moisture. In the case of alkylcarbonylaminotriazine mixtures, the individual components could be separated by means of HPLC (20 μl loop; UV detector (250 nm); 1 ml/min, acetonitrile: aqueous potassium dihydrogenphosphate (0.05 mol/l)=1:1; Purospher RP18e column). The amounts of components in the examples which follow are quoted in area percent (area %). The substances were identified by high-resolution mass spectrometry, in some cases in the form of a direct HPLC-MS coupling or by means of $^1H$ und $^{13}C$ nuclear resonance spectroscopy.

EXAMPLE 1

31.5 g (0.25 mol) of melamine, 1200 ml of butanol, 88.1 g (1 mol) of ethylene carbonate and 94.5 g (1.75 mol) of sodium methoxide (solid) were initially charged at a temperature of 20° C. Subsequently, the reaction mixture was heated to approx. 70° C. and stirred at approx. 70° C. for a further 120 minutes. After cooling the mixture to approx. 30° C., 367.6 g (1.75 mol) of 30% aqueous nitric acid were added with stirring. The aqueous phase was removed and the organic homogeneous phase was washed a further 3 times with 300 ml of water each time. Concentration of the organic phase resulted in a 50% by weight butanolic product solution which comprised predominantly 2,4,6-tris(butoxycarbonylamino)-1,3,5-triazine (30.2 area %), 2-methoxycarbonylamino-4,6-bis(butoxycarbonylamino)-1,3,5-triazine (35.5 area %), 2,4-bis(butoxycarbonylamino)-6-amino-1,3,5-triazine (7.3 area %), 2,4-bis(methoxycarbonylamino)-6-butoxycarbonylamino-1,3,5-triazine (12.1 area %), 2-butoxycarbonylamino-4-methoxycarbonylamino-6-amino-1,3,5-triazine (5.9 area %) and tris(methoxycarbonylamino)-1,3,5-triazine (4 area %) (HPLC, $^1H$, $^{13}C$ NMR).

EXAMPLE 2

Example 2 was carried out in a similar manner to example 1, except that the reaction temperature was 75° C. After 120 minutes, the reaction mixture comprised predominantly 2,4,6-tris(butoxycarbonylamino)-1,3,5-triazine (33.6 area %), 2-methoxycarbonylamino-4,6-bis(butoxycarbonylamino)-1,3,5-triazine (32.1 area %), 2,4-bis(butoxycarbonylamino)-6-amino-1,3,5-triazine (9.1 area %), 2,4-bis(methoxycarbonylamino)-6-butoxycarbonylamino-1,3,5-triazine (8.8 area %), 2-butoxycarbonylamino-4-methoxycarbonylamino-6-amino-1,3,5-triazine (5.3 area %) and tris(methoxycarbonylamino)-1,3,5-triazine (4.5 area %)

EXAMPLE 3

31.5 g (0.25 mol) of melamine, 112 ml of butanol, 88.1 g (1 mol) of ethylene carbonate and 151.3 g (1.75 mol) of sodium methoxide (solid) were charged at a temperature of 20° C. into a kneading reactor (List reactor). Subsequently, the reaction mixture was kneaded at 75° C. for 1 hour. Direct analysis of the reaction mixture allowed the main components of the mixture to be identified as 2,4,6-tris(methoxycarbonylamino)-1,3,5-triazine, 2-butoxycarbonylamino-4,6-bis(methoxycarbonylamino)-1,3,5-triazine and 2,4-bis(butoxycarbonylamino)-6-methoxycarbonylamino-1,3,5-triazine, 2,4,6-tris(butoxycarbonylamino)-1,3,5-triazine, (HPLC, HPLC-MS).

EXAMPLE 4

29 g (0.23 mol) of melamine, 976 ml of butanol, 81 g (0.92 mol) of ethylene carbonate and 87 g (1.61 mol) of sodium methoxide (solid) were initially charged at a temperature of 20° C. Subsequently, the reaction mixture was heated to approx. 70° C. and stirred at approx. 70° C. for a further 120 minutes. After cooling the mixture to approx. 30° C., 338 g (1.61 mol) of 30% aqueous nitric acid were added with stirring. The aqueous phase was removed and the organic homogeneous phase was washed a further 3 times with 300 ml of water each time. Concentration of the organic phase resulted in a 50% by weight butanolic product solution which comprised predominantly 2,4,6-tris(butoxycarbonylamino)-1,3,5-triazine (29.3 area %), 2-methoxycarbonylamino-4,6-bis(butoxycarbonylamino)-1,3,5-triazine (37.5 area %), 2,4-bis(butoxycarbonylamino)-6-amino-1,3,5-triazine (6.3 area %), 2,4-bis(methoxycarbonylamino)-6-butoxycarbonylamino-1,3,5-triazine (13.2 area %), 2-butoxycarbonylamino-4-methoxycarbonylamino-6-amino-1,3,5-triazine (5.8 area %) and tris(methoxycarbonylamino)-1,3,5-triazine (4.7 area %) (HPLC, $^1$H, $^{13}$C NMR).

EXAMPLE 5

29 g (0.23 mol) of melamine, 1200 ml of butanol, 72.9 g (0.83 mol) of ethylene carbonate, 8.3 g (0.09 mol) of dimethyl carbonate and 87.0 g (1.61 mol) of sodium methoxide (solid) were initially charged at a temperature of 20° C. Subsequently, the reaction mixture was heated to approx. 80° C. and stirred at approx. 80° C. for a further 120 minutes. After cooling the mixture to approx. 30° C., 338.2 g (1.61 mol) of 30% aqueous nitric acid were added with stirring. The aqueous phase was removed and the organic homogeneous phase was washed a further 3 times with 300 ml of water each time. Concentration of the organic phase resulted in a 50% by weight butanolic product solution which comprised predominantly 2,4,6-tris(butoxycarbonylamino)-1,3,5-triazine (27.3 area %), 2-methoxycarbonylamino-4,6-bis(butoxycarbonylamino)-1,3,5-triazine (33.9 area %), 2,4-bis(butoxycarbonylamino)-6-amino-1,3,5-triazine (6.9 area %), 2,4-bis(methoxycarbonylamino)-6-butoxycarbonylamino-1,3,5-triazine (12.6 area %), 2-butoxycarbonylamino-4-methoxycarbonylamino-6-amino-1,3,5-triazine (4.9 area %) and tris(methoxycarbonylamino)-1,3,5-triazine (8.0 area %) (HPLC, $^1$H, $^{13}$C NMR).

EXAMPLE 6

Example 6 was carried out analogously to example 1, except that 1200 ml of butanol were initially charged at 50° C. Subsequently, 31.5 g (0.25 mol) of melamine, 110.0 g (1.25 mol) of ethylene carbonate and 121.5 g (2.25 mol) of sodium methoxide (solid) were added. The reaction mixture was subsequently heated at 70° C. for 3 hours. The reaction mixture comprised a total of 88.4% triscarbonylaminotriazine compounds and approx. 9% dicarbonylaminotriazine compounds.

What is claimed is:
1. A process for preparing an alkoxycarbonylaminotriazine of the formula I:

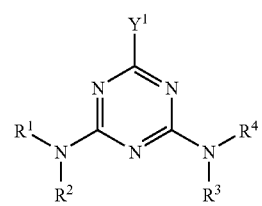

(I)

wherein
Y$^1$ is hydrogen, C$_1$-C$_4$-alkyl, phenyl optionally substituted by C$_1$-C$_4$-alkyl, C$_1$-C$_4$-alkoxy or halogen, or a radical of the formula NR$^5$R$^6$ and
R$^1$, R$^2$, R$^3$, R$^4$, R$^5$ and R$^6$ are each independently hydrogen or a radical of the formula COOX or X where X is C$_1$-C$_{13}$-alkyl whose carbon framework may be interrupted by 1 or 2 oxygen atoms in an ether function and/or be substituted by hydroxyl, or C$_3$-C$_6$-alkenyl,
with the proviso that at least one of the radicals R$^1$ to R$^4$ in formula I or, when Y$^1$ is NR$^5$R$^6$, at least one of the radicals R$^1$ to R$^6$ is COOX,
comprising:
reacting a triazine of the formula II:

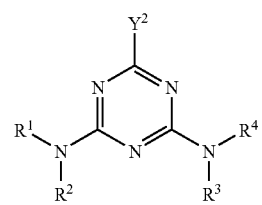

(II)

wherein
Y$^2$ is hydrogen, C$_1$-C$_4$-alkyl, amino or phenyl optionally substituted by C$_1$-C$_4$-alkyl, C$_1$-C$_4$-alkoxy or halogen, and
R$^1$ to R$^4$ are each as defined above,
with the proviso that, in formula II, when Y$^2$ is not amino, at least one of the radicals R$^1$ R$^4$ is hydrogen, with a cyclic carbonic ester-of the formula III in the presence of an alcohol and of a base,

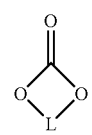

(III)

wherein
> L is ethylene, 1,2- or 1,3-propylene, or 1,2-, 1,4-, 2,3-, or 1,3-butylene, and also optionally with a minor amount of an acyclic carbonic ester of the formula IV
>
> $$Z^1\text{—}O\text{—}CO\text{—}OZ^2 \quad (IV)$$
>
> wherein
> $Z^1$ and $Z^2$ are each independently $C_1$-$C_8$-alkyl, and
>
> and a $C_1$-$C_{13}$-alkanol whose carbon framework may be interrupted by 1 or 2 oxygen atoms in an ether function and/or be substituted by hydroxyl, or a $C_3$-$C_6$-alkenol, in the presence of an alkali metal alkoxide or alkaline earth metal alkoxide as a base.

2. A process as claimed in claim 1, wherein a $C_1$-$C_{13}$-alkanol is used.

3. A process as claimed in claim 1, wherein the base is an alkali metal alkoxide.

4. A process as claimed in claim 1, wherein a cyclic carbonic ester of the formula III in which L is ethylene or 1,2-propylene is used.

5. A process as claimed in claim 1, wherein the reaction is carried out at a temperature of from 20 to 180° C.

6. A process as claimed in claim 1, wherein the reaction is carried out with from 1 to 50 mol of alkanol, based in each case on one molar equivalent of amino groups in the triazine of the formula II.

7. A process as claimed in claim 1, wherein the reaction is carried out with from 0.1 to 10 mol of cyclic carbonic ester, based in each case on one molar equivalent of amino groups in the triazine of the formula II.

8. A process as claimed in claim 1, wherein the reaction is carried out with from 0.1 to 10 molar equivalents of alkali metal alkoxide or alkaline earth metal alkoxide, based in each case on one molar equivalent of amino groups in the triazine of the formula II.

9. A process as claimed in claim 1, wherein triazine II and alkanol are initially charged and then, in any desired sequence, alkali metal alkoxide or alkaline earth metal alkoxide, in the solid state and/or dissolved in alkanol, and carbonic ester are metered in, and alkali metal alkoxide or alkaline earth metal alkoxide and carbonic ester can be metered in fully before the commencement of the reaction or partly before the commencement of the reaction and partly after the commencement of the reaction.

10. A process as claimed in claim 1, wherein from 0 to 25 mol % of the cyclic carbonic ester of the formula III may be replaced by an acyclic carbonic ester of the formula IV.

* * * * *